United States Patent

Kaule et al.

[11] 4,121,469
[45] Oct. 24, 1978

[54] METHOD AND APPARATUS FOR PRODUCING A PULSE TYPE ULTRASONIC WAVE ON A WORKPIECE SURFACE

[75] Inventors: Walter Kaule; Erik Primbsch, both of Cologne, Fed. Rep. of Germany

[73] Assignee: Krautkramer-Branson, Incorporated, Stratford, Conn.

[21] Appl. No.: 856,335

[22] Filed: Dec. 1, 1977

[30] Foreign Application Priority Data

Feb. 24, 1977 [DE] Fed. Rep. of Germany ....... 2707914

[51] Int. Cl.² ............................................. G01N 29/00
[52] U.S. Cl. ..................................................... 73/643
[58] Field of Search ......................... 73/643, 644, 71.5

[56] References Cited

U.S. PATENT DOCUMENTS 3,978,713  9/1976  Penney .................................... 73/643

Primary Examiner—James J. Gill
Attorney, Agent, or Firm—Ervin B. Steinberg; Philip J. Feig

[57] ABSTRACT

A method and apparatus for producing on the surface of a workpiece an ultrasonic pulse wave without physical contact comprise the use of a laser beam illuminating a small, striplike, portion of the workpiece surface and such portion being moved with uniform motion along a linear axis over a predetermined distance. The angle of propagation of the resulting ultrasonic wave is a function of the propagation velocity of sound in the workpiece and the velocity of the illuminated portion along the linear axis.

10 Claims, 3 Drawing Figures

METHOD AND APPARATUS FOR PRODUCING A PULSE TYPE ULTRASONIC WAVE ON A WORKPIECE SURFACE

BRIEF SUMMARY OF THE INVENTION

This invention concerns an apparatus and method for producing pulse type ultrasonic waves having a predetermined direction of propagation relative to the surface of light absorbing workpieces. The present invention is particularly applicable to the field of nondestructive testing of workpieces by ultrasound without physical contact between a laser producing a beam of coherent radiation and the workpiece being tested.

When testing with ultrasonic energy workpieces which are not accessible or accessible only with difficulty, including those exhibiting a hot surface, it is necessary to produce the ultrasonic energy directly on the surface or in layers disposed in close proximity to the surface of the workpiece. Producing ultrasonic energy directly on the workpiece surface is advantageous also when high relative speeds between a workpiece and a test station are present.

Electrodynamic, magnetic and thermal methods are known for producing ultrasonic energy directly in the workpiece. The thermal method utilizes light rays, preferably lasers, as an excitation means. When magnetic means are used, excitation across greater distances is not possible, the limit being generally a distance of a fraction of a millimeter. In the case of thermal or optical methods greater distances between the light source and the workpiece are possible. Suitable magnetic and thermal methods for producing ultrasonic energy are described in the book by J. and H. Krautkramer, Werkstoffprufung mit Ultraschall, 3rd edition 1975, Springer Verlag, Berlin/Heidelberg, pages 148 to 151 and 153 to 162. Testing at distances up to several meters is possible when laser energy beams of high intensity are used.

It is an object of the present invention to provide ultrasonic search energy in a workpiece by the use of the optical thermal effect without the need for physical contact between the source of optical energy and the workpiece.

Another object of the invention is the provision of means for causing the ultrasonic energy to be propagated along a predetermined angle relative to an axis normal to the workpiece surface.

In accordance with the present invention, it is proposed that a strip-like portion of the workpiece surface to be excited is illuminated by a beam of laser energy, the workpiece portion corresponding to the cross section of the beam. The surface to be excited is that portion of the workpiece surface into which ultrasonic energy is to be transmitted. The geometric shape of the surface to be excited is determined by the test problem. For ultrasonic testing such surface generally has a size of several square centimeters, and typically a strip-like surface portion illuminated by the laser beam is moved at a uniform speed transverse to its length across the surface to be excited. The pulse duration of the laser beam must be equal to the interval of translational motion. Such interval is derived as a function of the length of the total surface to be excited in the direction of motion and the speed at which such motion occurs. The velocity of motion is dependent upon the direction of propagation of the ultrasonic wave produced and the velocity of propagation of the wave in the workpiece. The surface portions of the workpiece illuminated by the laser beam are subjected to a localized thermal expansion on account of the absorption of beam energy. As a result, local mechanical stresses are caused in the material and such stresses propagate in an elastic manner, producing an acoustic wave. The depth of penetration of the laser beam must be negligibly small in relation to the ultrasonic wavelength produced and the duration of the laser pulse must be short in relation to the time period of the ultrasonic wave.

A preferred embodiment of the present invention will be described in the following specification which should be read in conjunction with the accompanying drawings.

DETAILED DESCRIPTION OF THE INVENTION

Figure 1:
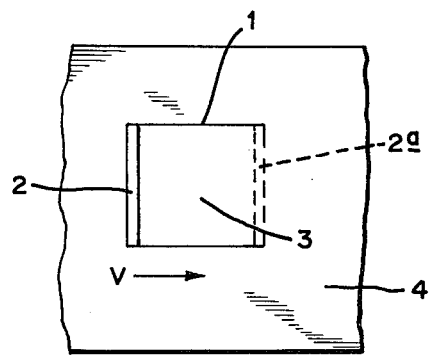
FIG. 1 is a schematic plan view of a workpiece surface to be excited.
Figure 2:
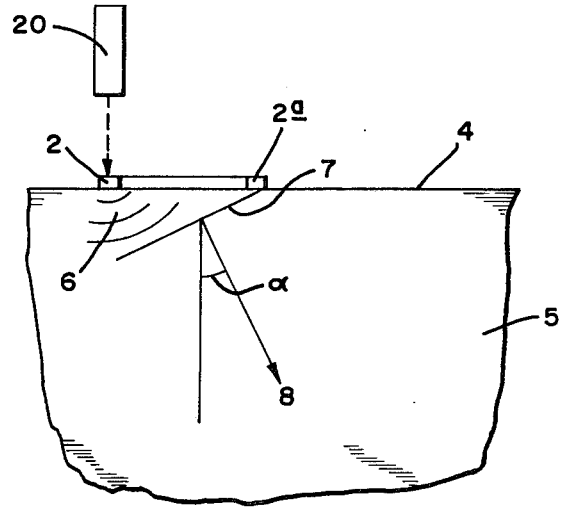
FIG. 2 is a schematic elevational view of the workpiece showing the propagation of the ultrasonic wave.

Referring to the figures and FIGS. 1 and 2 in particular, it is desired that surface portion 3 of 2 cm by 2 cm of the workpiece 5 be excited with an ultrasonic shock wave utilizing a laser beam. The workpiece 5 is steel having an acoustic propagation velocity for longitudinal sound waves of 6,000 m/sec and an acoustic velocity for surface waves of 2,987 m/sec. It is desired, moreover, that the longitudinal wave propagate in a direction of 45° to the perpendicular axis intersecting the workpiece surface and in another example that an acoustic surface wave be produced.

The laser 20 provides a beam of coherent light initially upon the small surface portion 2, FIG. 1. Responsive to relative motion, the illuminated portion 2 is moved during a time interval $t$ at a velocity $v$ in the direction of the surface edge line 1. FIG. 2 illustrates such motion, showing that the narrow strip 2 illuminated initially and shown raised for the sake of clarity has been moved at a velocity $v$ across the surface 4 to become disposed at the end position 2a. In this manner, all surface portions along the path of relative motion become excited continuously in sequence for producing, in accordance with the known Huygens' principle, a fundamental wave. The production of the ultrasonic wave occurs as the result of the previously mentioned localized thermal expansion.

On account of interferences indicated by numeral 6 and consonant with known physical principles there is produced a plane wave front which is propagated at the angle $\alpha$ along the direction of arrow 8. The intermediate lines indicated within the region 6 are meant to represent the not simultaneously present wave fronts, but represent the wave fronts propagated per unit of time, i.e. within the time domain, inasmuch as the instant invention concerns an ultrasonic shock wave and not a wave comprising several wave trains.

The relation between the individual values is given by known physical laws. Letter $v$ shall define the translational speed of the laser light strip, $c$ is the propagation velocity of the sound wave, $d$ is the length of the edge 1 in FIG. 1, that is, the distance from strip 2 to 2a in FIG. 2, and $t$ is the duration of the beam motion of strip 2. Hence:

$$v = d/t$$

When the motion of the beam is terminated, that is, when wave front 7 is disposed in the center of the excited strip 2a, the wave front, originating at the center of strip 2, has traveled the distance $c \times t$. Therefore:

$$c \times t = d \times \sin \alpha$$
$$\text{and } t = d \times \sin \alpha / c$$
$$\text{since } v = d/t; v = c/\sin \alpha.$$

For a given angle $\alpha$ the value $v$ can be calculated. In the present example angle $\alpha$ has been selected to be 45°. For the value $d = 2$ cm, the value $v$ becomes:

$$v = \frac{6 \times 10^3 \text{ m/sec}}{\sin 45°} = 8,485 \text{ m/sec}$$

and the laser beam pulse duration, which equals the motion time, $$t = 2.4 \ \mu\text{sec}.$$

If a surface wave is to be generated the angle $\alpha$ must equal 90 degrees. Hence, $$v = 2,897 \text{ m/sec}$$

and $t = 6.7 \ \mu\text{sec}$.

Figure 3:
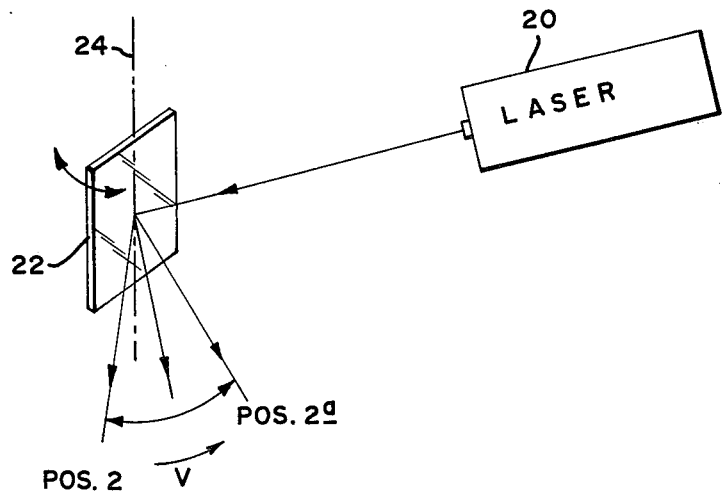
FIG. 3 is a schematic illustration describing the deflection of the laser beam as required for the present invention.

Motion of the beam across the predetermined workpiece surface is obtainable by several different arrangements. As shown in FIG. 3, the laser source 20 directs its beam toward a mirror 22 mounted for pivotal motion about an axis 24. Responsive to pivotal motion of the mirror 22, the laser beam is subjected to motion from position 2 to position 2a. Such motion occurs at the velocity $v$ defined above. In another embodiment laser beam deflection is obtained by the diffraction of the laser beam by means of an ultrasonic wave in a crystal, utilizing an electrical signal for signal deflection. Such a device disposed in the light beam is commercially available under the name Acousto Optic Laser Deflector from Soro Electro Optics, 92100 Boulogne Seine, France or from Laser-Optronic, Munich 50, West Germany.

The laser beam is shaped to the preferred strip form by known optical lens means, typically a pair of crossed cylinder lenses or alternatively, a single cylinder lens and masking means can be used to derive the rectangular beam shape.

When utilizing the above described arrangement for testing workpieces by the ultrasonic pulse echo method for defects, the ultrasonic echo signal resulting from the induced transmit signal can be sensed either by direct contact with the workpiece surface using a piezoelectric receiving probe or can be sensed in a contact free manner by a transit time interferometer arrangement as shown in Krautkramer supra, page 172, or in U.S. Pat. No. 4,046,477, dated Sept. 6, 1977 issued to W. Kaule, entitled "Interferometric Method and Apparatus for Sensing Surface Deformation of a Workpiece Subjected to Acoustic Energy".

What is claimed is:

1. The method of producing free of physical contact on the surface of a light absorbing workpiece an ultrasonic pulse wave having a predetermined angle of propagation relative to the workpiece surface comprising:
   illuminating a portion of the workpiece surface with a beam of coherent radiation;
   causing such illuminated portion to be moved in uniform motion at a predetermined velocity along a linear axis over a predetermined distance, and
   selecting said predetermined velocity to provide said predetermined angle of propagation as determined also by the propagation velocity of said wave in the workpiece.

2. The method of producing free of physical contact on the surface of a light absorbing workpiece an ultrasonic pulse wave having a predetermined angle of propagation relative to the workpiece surface comprising:
   illuminating a portion of the workpiece surface with a beam of coherent radiation;
   causing such illuminated portion to be moved in uniform motion at a predetermined velocity along a linear axis over a predetermined distance;
   whereby the ultrasonic pulse wave results from the superposition of fundamental waves and the angle $\alpha$ of propagation of the wave relative to an axis normal to the workpiece surface is given by the equation: $\sin \alpha = c/v$;
   wherein $c$ is the propagation velocity of the ultrasonic wave in the workpiece and $v$ is the velocity of the illuminated portion along said linear axis.

3. The method of producing free of physical contact an ultrasonic pulse wave as set forth in claim 2, said portion of the workpiece comprising a strip-like portion, and said linear axis being transverse to the longitudinal axis of said strip-like portion.

4. The method of producing free of physical contact an ultrasonic pulse wave as set forth in claim 3, said strip-like portion being of substantially rectangular shape.

5. An apparatus for producing an ultrasonic pulse wave on the surface of a workpiece, said wave having a predetermined angle of propagation relative to an axis normal to the workpiece surface comprising:
   means for providing a beam of coherent radiation disposed for illuminating a portion of a workpiece surface, and
   means for causing said illuminated portion to be moved lineally along said workpiece surface with a predetermined uniform velocity and over a predetermined distance, said predetermined velocity being responsive to said angle and to the velocity of propagation of said ultrasonic wave in the workpiece.

6. An apparatus for producing an ultrasonic pulse wave on the surface of a workpiece, said wave having a predetermined angle of propagation relative to an axis normal to the workpiece surface comprising:
   laser means for providing a beam of coherent radiation disposed for illuminating a strip-like portion of a workpiece surface;
   means for causing said illuminated strip-like portion to be moved lineally along said workpiece surface with a predetermined uniform velocity and over a predetermined distance, whereby said predetermined velocity $v$ is determined by: $\sin \alpha = c/v$
   wherein $\alpha$ is said angle of propagation of the ultrasonic wave and $c$ is the propagation velocity of the ultrasonic wave in the workpiece.

7. An apparatus for producing an ultrasonic pulse wave on the surface of a workpiece as set forth in claim 6, said strip-like portion is of substantially rectangular shape, and said means for causing said portion to be moved causing such motion in a direction transverse to the longitudinal axis of said strip portion.

8. An apparatus for producing an ultrasonic pulse wave on the surface of a workpiece as set forth in claim 6, said means for causing said illuminated strip-like portion to be moved comprising deflection means disposed between said laser means and the workpiece surface for deflecting said beam of coherent radiation along the surface of the workpiece.

9. An apparatus for producing an ultrasonic pulse wave on the surface of the workpiece as set forth in claim 8, said deflection means being a movable mirror surface.

10. An apparatus for producing an ultrasonic pulse wave on the surface of a workpiece as set forth in claim 8, said deflection means comprising an acousto-optical deflecting means.

* * * * *